(12) United States Patent
Pillai (10) Patent No.: US 11,103,250 B2
(45) Date of Patent: Aug. 31, 2021

(54) ANEURYSM OCCLUDER

(71) Applicant: Jayandiran Pillai, Johannesburg (ZA)

(72) Inventor: Jayandiran Pillai, Johannesburg (ZA)

(73) Assignee: Jayandiran Pillai, Johannesburg (ZA)

( * ) Notice: Subject to any disclaimer, the term of this patent is extended or adjusted under 35 U.S.C. 154(b) by 0 days.

(21) Appl. No.: 15/772,371

(22) PCT Filed: Oct. 27, 2016

(86) PCT No.: PCT/IB2016/056470
§ 371 (c)(1),
(2) Date: Apr. 30, 2018

(87) PCT Pub. No.: WO2017/072692
PCT Pub. Date: May 4, 2017

(65) Prior Publication Data
US 2018/0317930 A1    Nov. 8, 2018

(51) Int. Cl.
*A61B 17/12* (2006.01)

(52) U.S. Cl.
CPC .... *A61B 17/12113* (2013.01); *A61B 17/1215* (2013.01); *A61B 17/12031* (2013.01); *A61B 17/12177* (2013.01)

(58) Field of Classification Search
CPC ........ A61B 17/12113; A61B 17/12118; A61B 17/1215; A61B 17/12031; A61B 17/12027; A61B 17/12177; A61B 17/12168; A61B 17/12172; A61B 17/12022; A61B 17/12036; A61B 17/12122; A61B 17/12109; A61B 17/12104; A61B 17/12099; A61B 17/12045; A61B 17/1204; A61B 17/1205; A61B 17/12163; A61B 17/12154; A61B 17/12145; A61B 17/1214; A61B 17/12131; A61B 17/0057;
(Continued)

(56) References Cited

U.S. PATENT DOCUMENTS

| 7,153,323 B1 * | 12/2006 | Teoh ................. A61B 17/12022 623/1.23 |
| 2004/0193246 A1 * | 9/2004 | Ferrera ............ A61B 17/12022 623/1.15 |

(Continued)

FOREIGN PATENT DOCUMENTS

| WO | WO 2008/156464 | 12/2008 |
| WO | WO 2013/005195 | 1/2013 |

OTHER PUBLICATIONS

International Search Report and Written Opinion for PCT/IB2016/056470 dated Jan. 27, 2017 (8 pages).

(Continued)

*Primary Examiner* — Diane D Yabut
(74) *Attorney, Agent, or Firm* — Sheppard Mullin Richter & Hampton LLP (57) ABSTRACT

This invention relates to an aneurysm occluder, and more particularly but not exclusively, to an endovascular aneurysm occluder that can be inserted into an aneurysm cavity by using endovascular surgical procedures. The aneurysm occluder, includes a resiliently deformable cage (2) made of a mesh structure in which the mesh structure is cylindrical in cross section and closed off at opposite ends, where the opposite ends are held and closed off with shanks (4).

9 Claims, 9 Drawing Sheets

(58) Field of Classification Search
CPC ........... A61B 2017/12127; A61B 2017/00619;
A61B 2017/00606; A61B 2017/00597;
A61B 2017/00592; A61B 2017/00646;
A61B 2017/00641; A61B 2017/00637;
A61B 2017/00632; A61B 2017/00623
See application file for complete search history.

(56) References Cited

U.S. PATENT DOCUMENTS

| | | | | |
|---|---|---|---|---|
| 2015/0297240 | A1* | 10/2015 | Divino | A61B 17/12177 606/200 |
| 2016/0030050 | A1* | 2/2016 | Franano | A61B 17/12031 606/195 |

OTHER PUBLICATIONS

Austermann, "AndraTec PilloW a Novel AAA Sac Occlusion First European Experience Case Report in Thoracal Aortic Dissection at St. Franziskus Hospital, Germany", Clinical News Bulletin, Nov. 2014, 2 pages.

Massmann et al., "Multiple Treatment Approaches Following Incomplete Endovascular Closure of Abdominal Aneurysm Rupture-Related Aorto-Caval Fistula", *EuroIntervention*, 2018, Abstract, 1 page.

\* cited by examiner

ANEURYSM OCCLUDER

CROSS REFERENCE TO RELATED APPLICATIONS

This application is a U.S. National Stage Application under 35 U.S.C. 371 of International Application No. PCT/IB2016/054670 filed Oct. 27, 2016, which application claims priority to South Africa Application No. 2015/02865, filed Oct. 28, 2015, the contents of which are hereby incorporated by reference in their entirety into the present disclosure.

FIELD OF THE INVENTION

This invention relates to an aneurysm occluder, and more particularly but not exclusively, to an endovascular aneurysm occluder that can be inserted into an aneurysm cavity by using endovascular surgical procedures.

BACKGROUND TO THE INVENTION

An aneurysm is an excessive expansion of a wall segment of an artery and occurs when a wall segment of an artery weakens. Blood pressure in the artery creates the swelling at the weakened wall section. The swelling is commonly referred to as an aneurysm cavity or aneurysm sac. As the size of the aneurysm increases, the risk of rupture increases. A rupture can cause internal bleeding which may result in severe complications and even death.

Endovascular Aneurysm Repair or Endovascular Aortic Repair ("EVAR") is a widely accepted corrective surgical procedure to repair an aneurysm of the aorta (abdominal or thoracic). The procedure involves insertion of a vascular prosthesis, commonly referred to as a stent graft or graft device. The graft device is tubular and provides an artificial lumen for blood to flow, replacing, or locating inside, the damaged artery, thereby immediately taking pressure off of the damaged portion of the blood vessel. The procedure is performed percutaneously by, for example, making two small incisions in the groin to expose the femoral arteries and feeding a synthetic stent graft through these arteries, with catheters and guide-wires, until the stent graft is positioned. The damaged and expanded part of the blood vessel is internally lined by the stent graft and the stent graft attaches, by radial force at either end to the normal, healthy portions of proximal and distal arteries.

The vascular prosthesis must be attached to the blood vessel in such a way that there is a strong, tight seal around the normal, healthy proximal and distal artery so that blood will not escape into the aneurysm sac. In practice, it is often difficult to attach the stent graft to the ends of the blood vessel in such a way that there is a permanent strong, tight seal between the proximal and distal artery and opposing ends of the stent graft and, as a result, blood flow into the aneurysm sac ("endoleak") may occur. An endoleak may occur in up to 20% of all cases and is considered to be a failure of treatment and may be life-threatening.

Endoleak can be treated in a variety of ways. One way to treat endoleak is by open surgical repair and complete replacement of the stent graft. Open surgical repair and the insertion of a new graft carry a high operative mortality rate. Inducing thrombosis in the aneurysm sac is often a successful alternative way of treating the endoleak.

Thrombosis can be induced by injecting a liquid embolic agent, containing a biocompatible polymer, into the endoleak sac. Thrombosis can also be induced in aneurysms by a procedure called endovascular coiling. Endovascular coiling involves packing platinum coils into the aneurysm sac, through a catheter, to restrict blood circulation thereby inducing thrombosis.

A disadvantage of injecting a liquid embolic agent into the aneurysm sac is that the biocompatible polymer dissolves over time and is absorbed into the blood stream. A disadvantage of endovascular coiling is that aneurysms are often incompletely treated and carry a risk of aneurysm recurrence. In addition, coils are smaller in size to the aneurysm sac and may not fill the aneurysm sac completely.

United states patent application number US 2011/0054519 A1 in the name of Malte Neuss entitled "Device for closing defects in the vascular system" discloses a self-expanding device, particularly an implant, for closing defect openings in the human or animal body, which device, in a first state, has the shape of an elongated tube with slotted segments and in a second state has a shortened shape with formation of at least one open or substantially closed hollow structure of considerable transverse extent, where in the slotted segments of the tube form individual webs that are each connected to adjacent webs such that a net-like overall structure is obtained in the second state. The device described in this patent is for treating (closing) Atrial Septal Defects (ASD) or patent foramen ovate (PFO). ASD is a form of a congenital heart defect in which blood flows between the normally separated two upper chambers, the atria of the heart. The atria are separated by a dividing wall, the inter-atrial septum. If this septum is defective or absent, then oxygen-rich blood can flow directly from the left side of the heart to mix with the oxygen-poor blood in the right side of the heart, or vice versa. This can lead to lower-than-normal oxygen levels in the arterial blood that supplies the brain, organs, and tissues. An ASD may not produce noticeable signs or symptoms, especially if the defect is small. An ASD may be caused when the foramen ovale does not close properly after birth. During development of the fetus, the interatrial septum develops to separate the left and right atria. However, a hole in the septum called the foramen ovale, allows blood from the right atrium to enter the left atrium during fetal development. This opening allows blood to bypass the nonfunctional fetal lungs while the fetus obtains its oxygen from the placenta. A layer of tissue called the septum primum acts as a valve over the foramen ovale during fetal development. After birth, the pressure in the right side of the heart drops as the lungs open and begin working, causing the foramen ovale to close entirely. In approximately 25% of adults, the foramen ovale does not entirely seal. In these cases, any elevation of the pressure in the pulmonary circulatory system (due to pulmonary hypertension, temporarily while coughing, etc.) can cause the foramen ovale to remain open. This is known as a patent foramen ovale (PFO), which is a type of atrial septal defect. Furthermore, the devices described herein are relatively small and are meant to fill a small defect or "hole" by constricting itself into the "hole" like a meshed plug. It does not include internal large shelves or plates that are spaced apart by 2 to 3 cm thereby providing multiple barriers to blood flow. Once these devices are in their deployed state it is a constricting mesh that provides resistance to bloom flow rather than a large set of multiple deformable plates. In its deployed state the device restricts blood flow by Constricting and tightening an external mesh rather than an expanded system of multiple internally placed plates. The devices described in this patent application are used to close a hole in a membrane and not to enhance thrombosis in an aneurysm sac. The device are not intended for and are not suitable for placement in an aneurysm sac.

United States patent application number US 2011/0152993 A1 in the name of Sequent Medical Inc., entitled "Multiple layer filamentary devices or treatment of vascular defects" discloses devices and methods for treatment of a patient's vasculature with some embodiments configured for delivery with a micro-catheter for treatment of the cerebral vasculature of a patient. Some embodiments may include a permeable shell and inner structure configured to occlude blood flow there-through. The devices disclosed in this patent application are directed to blocking a flow of fluid through a tubular vessel or into a small interior chamber of a saccular cavity or vascular defect within a mammalian body. More specifically, the embodiments disclosed are directed to devices and methods for treating a vascular defect of a patient including some embodiments directed specifically to the treatment of cerebral aneurysms of patients. As is the case with the devices referred to in the previous patent discussed above, there are no additional or different material thrombotic enhancement devices or agents inside the devices described in this patent application.

International patent application publication number WO 2013/005195 A1 published under international application number PCT/162012/053483 entitled "Aneurysm occluder" discloses an endovascular aneurysm occluder that can be inserted into an aneurysm cavity by using endovascular surgical procedures. The occluder enhances thrombosis of an aneurysm cavity and includes a housing consisting of a plurality of strands woven to form a mesh; a 1st securing means located at an end of the housing for gathering and securing the strands together; and a plurality of this shaped inserts located within the housing and secure to the housing. The disc shaped inserts enhances the occlusion of the aneurysm cavity.

OBJECT OF THE INVENTION

It is an object of this invention to provide an aneurysm occluder which, at least partially, alleviates some of the abovementioned difficulties.

SUMMARY OF THE INVENTION

In accordance with this invention there is provided an aneurysm occluder, comprising of a resiliently deformable cage made of a mesh structure in which the mesh structure is cylindrical in cross section and closed off at opposite ends, where the opposite ends are held and closed off with shanks.

There is further provided for the mesh strands to be double strands.

A still further feature of the invention provides for the cage to have a frame insert.

A further feature provides for the frame insert to be a substantially rectangular frame, having sheet material attached therein, with the frame bent to form a number of distinct sections.

The frame is resiliently deformable from its bent condition so that it forms the distinct sections. This is achieved through a manufacturing process, as is known in the art.

The cage further includes sheet inserts at its opposite ends.

These sheets are made of any flat sheet material made from, preferably, polyurethane or ptfe. In this specification the sheets are also referred to as plates.

Each shank terminates at its outer end in a bulbous gripping member.

The bulbous gripping members facilitate the grasping by clawed forceps during delivery.

This invention extends to a method of manufacturing an aneurism occluder comprising the steps of providing the closed off double strand mesh cage with shanks and inserting a formable frame insert therein.

These and other features of the invention are described in more detail below.

BRIEF DESCRIPTION OF DRAWINGS

One embodiment of the invention is described below, by way of example only, and with reference to the accompanying drawings in which.

DETAILED DESCRIPTION OF THE DRAWINGS

With reference to the drawings, an aneurysm occluder is generally indicated by reference numeral 1.

The aneurysm occluder 1 has a deformable housing or cage 2 which consists of a plurality of metallic strands woven to form a mesh. The strands may be stainless steel of nickel titanium (Nitinol). The mesh is tubular and has closed off ends to be generally sausage shaped in a relaxed position. The strands of the mesh are secured in stainless steel shanks (or securing means) at oppose ends of the cage. The shanks act as dot markers on an X-ray display to assist with insertion of the occluder during an operation.

The occluder 1 further has first securing means 3 which is located at a first end of the housing 2. The securing means, secures at its outer end 3, to an applicator's operational end, which would be an end of a guide wire in a catheter tube 11. A screw threaded end of the guide wire screws into a blind bore 4 in the securing means. The blind bore 4 is co-axial with the main axis of the housing 2. An insert 3 is located within the housing 2. The insert is not secured to the housing as its resilient frame holds it in place when it expands, as is described below.

The housing is biased to its relaxed tubular shape and may be compressed to take the shape of an inside of a catheter tube 11 or aneurysm sac 12 in which it is placed.

The insert 3, is made of a thin polytetraflouroethylene sheet or membrane 5. At its periphery, the membrane 5 is attached to a frame 6. The frame 6 is a closed loop wire made of nitinol. It will be appreciated by those skilled in the art that other suitable material may be used for the membrane such as polyurethane.

Nickel Titanium (NiTi) is a shape memory alloy also commonly referred to by its trade name, Nitinol. Above its transformation temperature, Nitinol is superelastic, able to withstand a large amount of deformation when a load is applied and return to its original shape when the load is removed. Below its transformation temperature, it displays the shape memory effect. When it is deformed it will remain in that shape until heated above its transformation temperature, at which time it will return to its original shape.

Nitinol is typically composed of approximately 55% Nickel by weight. Making small changes in the composition, can change the transition temperature of the alloy significantly. For this reason, Nitinol may or may not be superelastic at room temperature. These unique properties and tailorability of Nitinol to be used in a wide range of temperatures makes it suitable for many applications, particularly in medicine.

Nitinol is a shape memory alloy (SMA, also known as a smart alloy or memory metal or muscle wire) that "remembers" its geometry. After a sample of SMA has been deformed from its original crystallographic configuration, it regains its original geometry by itself during heating (one-way effect) or, at higher ambient temperatures, simply during unloading (pseudo-elasticity or superelasticity). These extraordinary properties are due to a temperature-dependent martensitic phase transformation from a low-symmetry to a highly symmetric crystallographic structure.

The membrane may be glued or sutured to the frame. In a preferred embodiment, the membrane is glued to the frame with "its own" PU.

In use, the occluder 1 is attached to the end of a guide wire, deformed and placed in a catheter tube. The deformation causes the housing and frame to collapse. The occluder 1 is then placed in the aneurysm cavity using the catheter as is known in the art. The occluder is allowed to expand and fill the cavity taking up the shape of the cavity. The mesh housing 2 takes the shape of the cavity insofar as it fits inside the cavity and the insert expands inside the housing.

Two occluders are inserted in an aneurysm sac.

The material used is nitinol 0.1 mm woven as a double strand to create a mesh. The double strand increases radial expansion so that the deployed device opens up within the aneurysm sac. Hence 48 X2 sets of wires can be used to construct a device that is 8 cm long. The wires are woven into a smooth shoulder distally to fit into the neck of the aneurysm sac. The round cylinder shape was created to fit into the aneurysm sac as well as to mould around the stent graft. The proximal and distal ends of the device (nitinol wires) are captured by a stainless steel shank. This aids visualization of the device on x-ray, when inserted. The stainless steel ends are more visible than the nitinol strands and appear as 2 "dot markers" on x-ray.

The plates have a nitinol frame and are joined together (as shown). The plates may be ptfe or p.u: The frame ensures expansion of the plates when deployed. The plates and frames are connected to each other to maintain position within the nitinol cage as well as to aid pushability of the device as it passes along the sheath during deployment. The plates and frame are made as a separate unit from the nitinol cage. It may be attached to the cage at either end. This again allows for stability of the plate position after deployment as well as aids pushability during deployment.

The proximal and distal surfaces of the cage may be covered by additional layers of thin p.u. These layers may be inserted, and may be attached, on an inside surface of the opposite proximal and distal ends of the cage. Hence a total of 5 p.u. plates aid thrombogenicity: 2 at either end of the cage and 3 internally lined as a separate framed piece.

Figure 1:
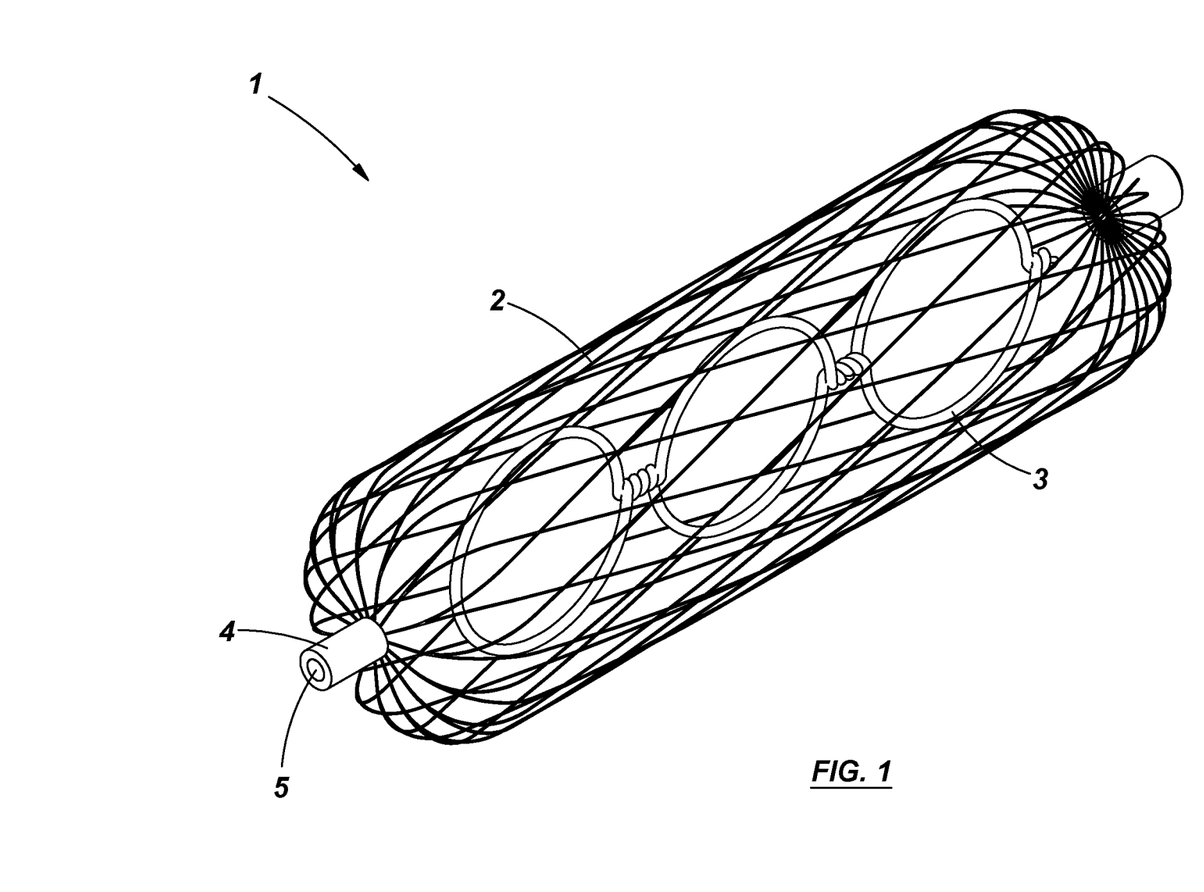
FIG. 1: is a perspective view of a first embodiment of an aneurysm occluder in accordance with the present invention.
Figure 2:
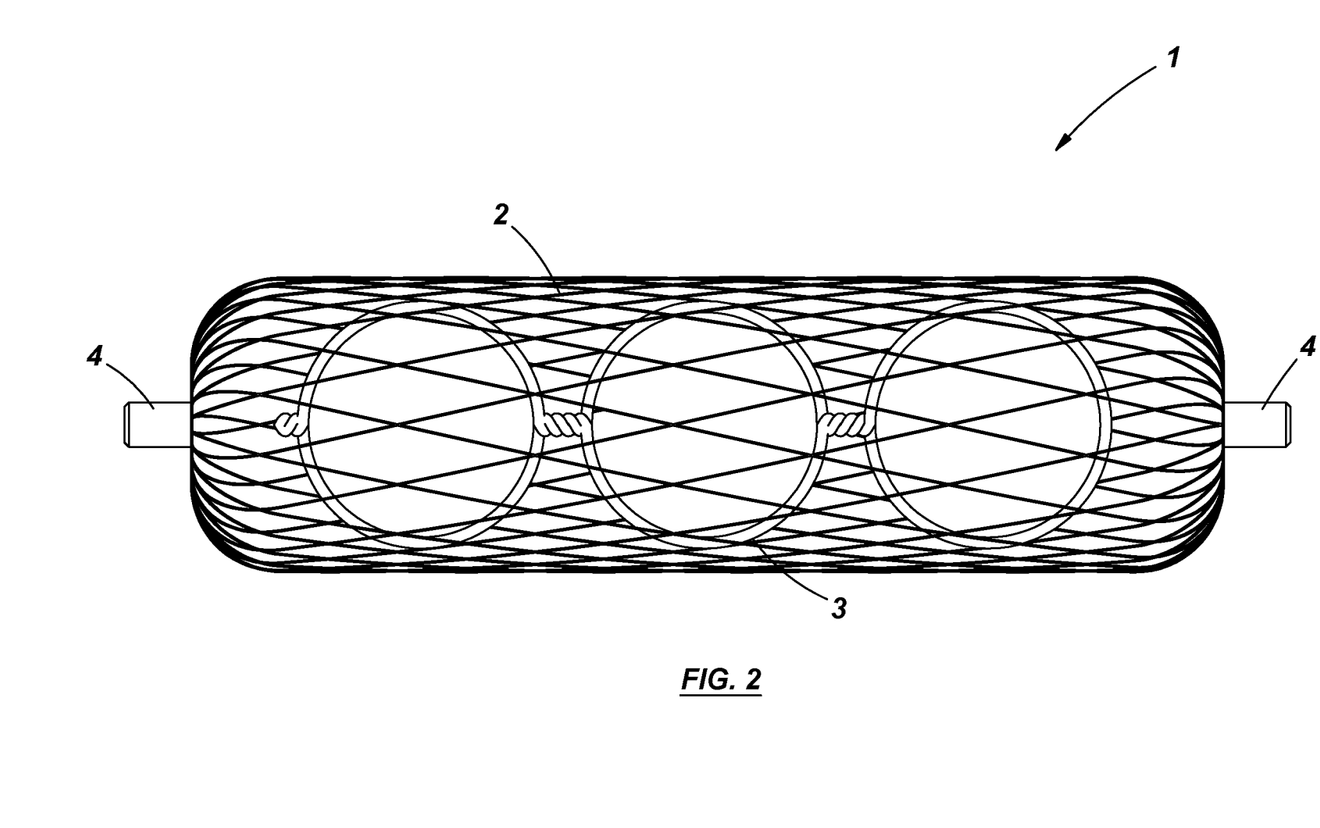
FIG. 2: is a side view of the aneurysm occluder of FIG. 1.
Figure 3:
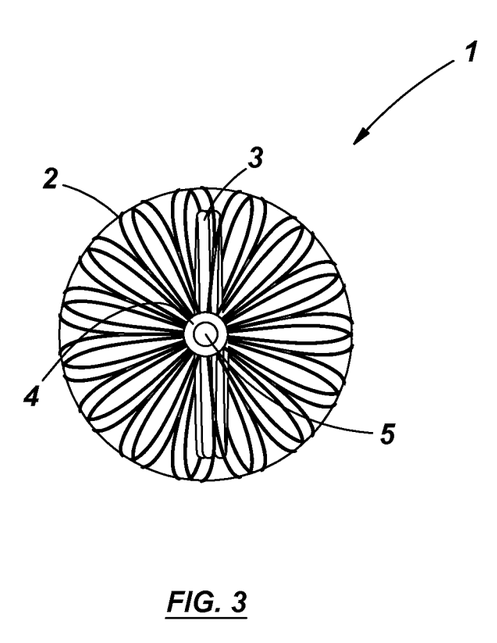
FIG. 3: is an end view of the aneurysm occluder of FIGS. 1 and 2.
Figure 4:
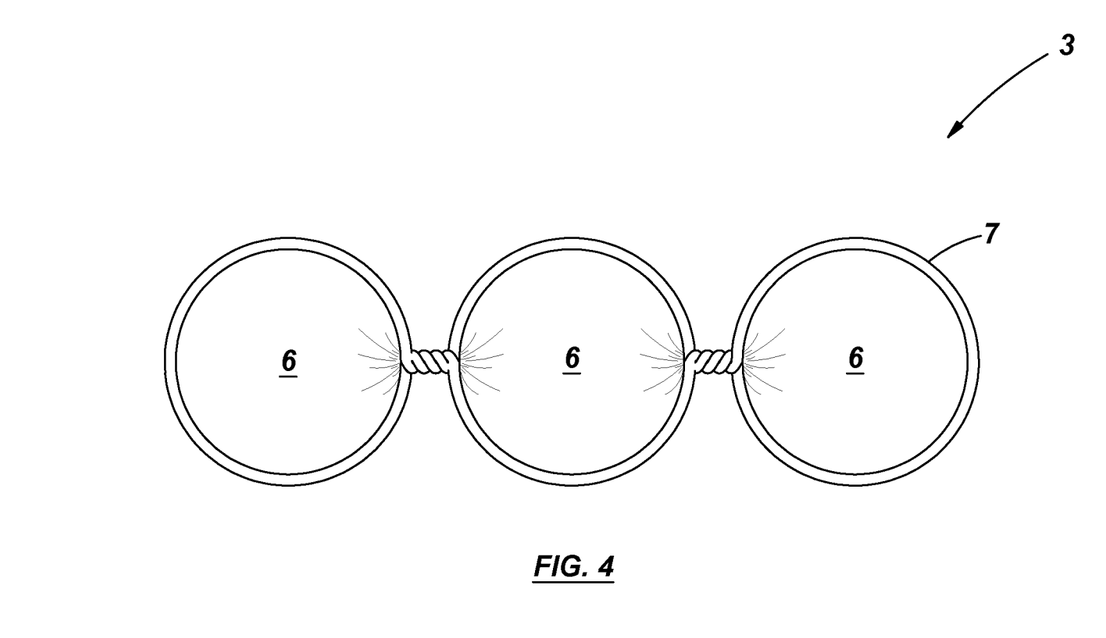
FIG. 4: is a side view of a first embodiment of an insert of the aneurysm occluder of FIGS. 1 to 3.
Figure 5:
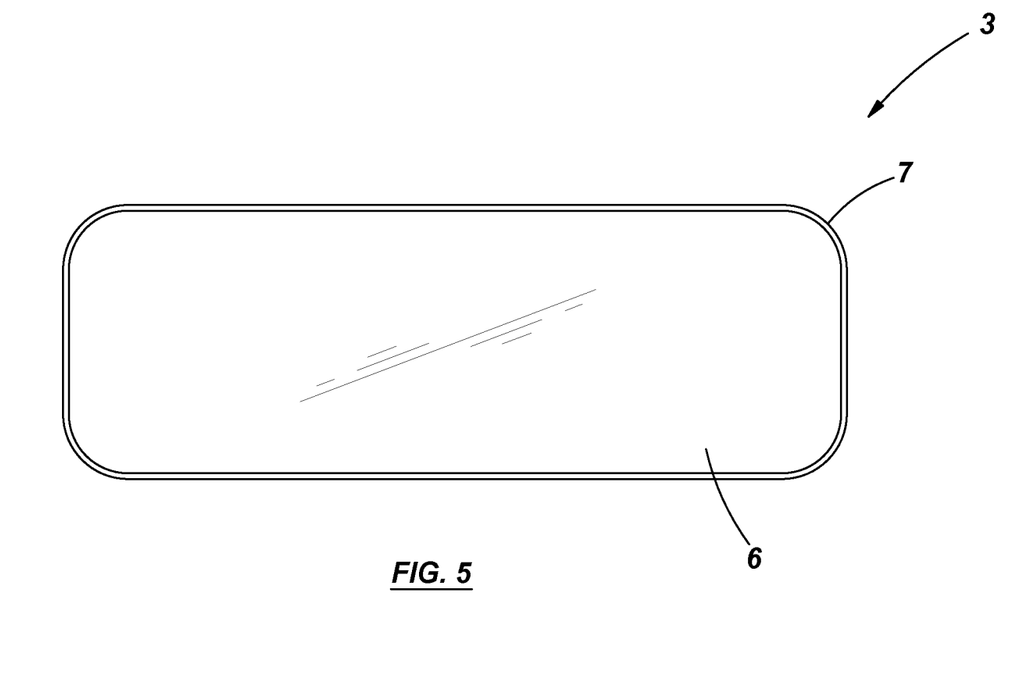
FIG. 5: shows a plan view of the insert of FIG. 4 before it is shaped and placed inside housing of the aneurysm occluder.
Figure 6:
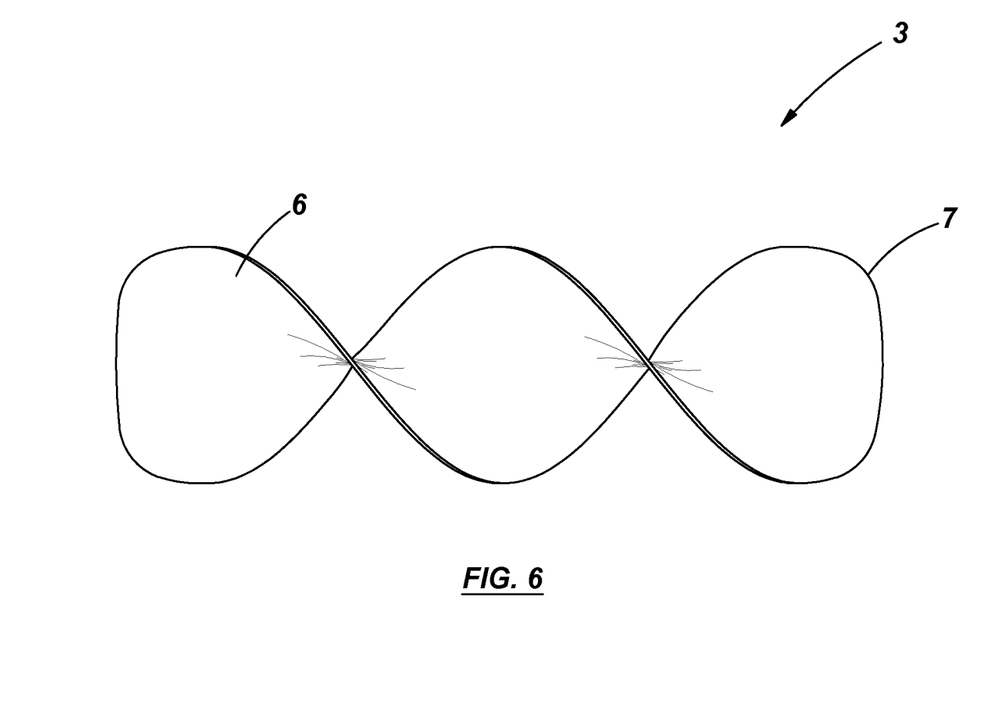
FIG. 6: shows a second embodiment of an insert of the aneurysm occluder of FIGS. 1 to 3.
Figure 7:
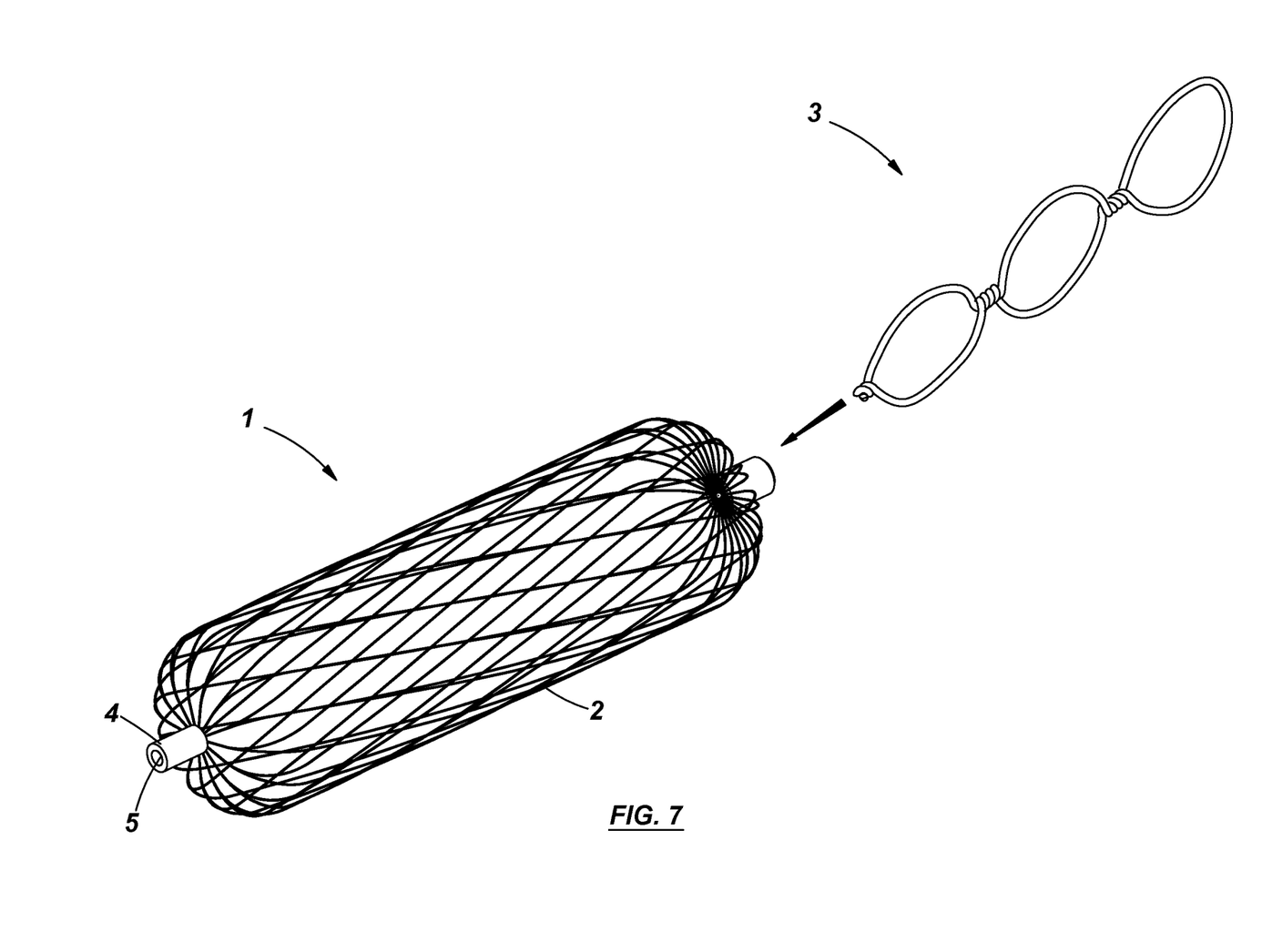
FIG. 7: shows a first step in a method of inserting the insert into the housing of the aneurysm occluder.
Figure 8:
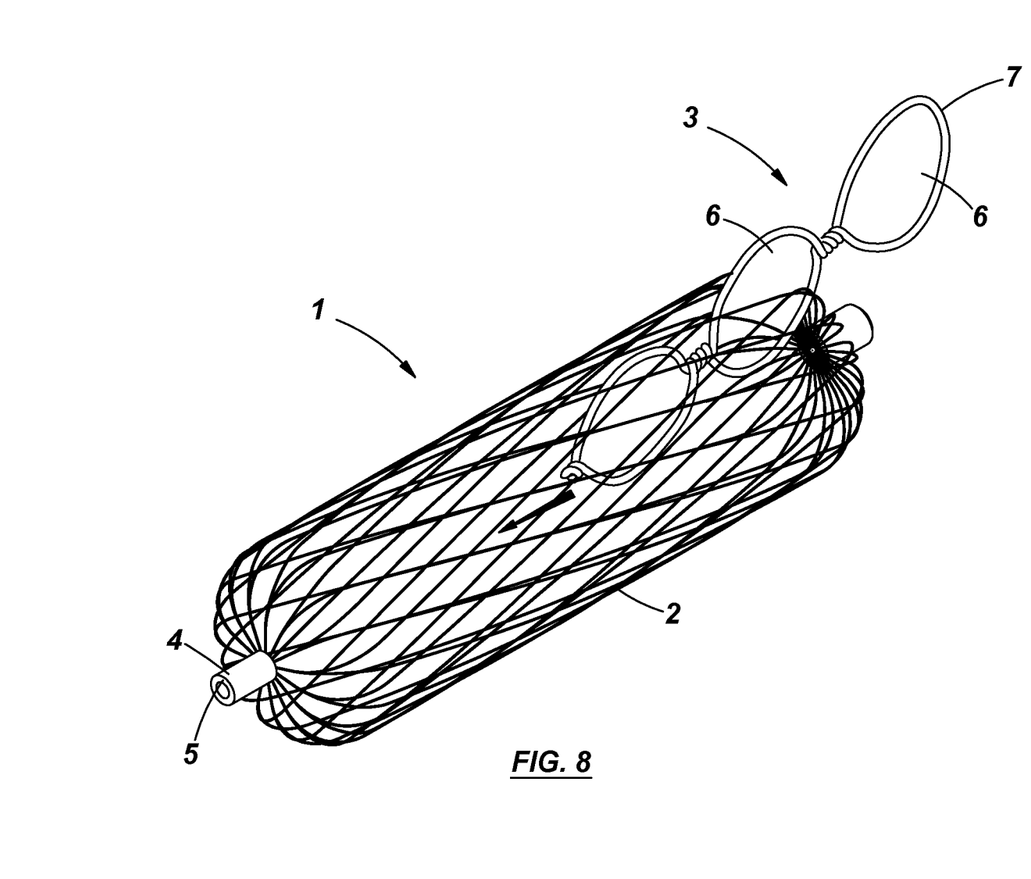
FIG. 8: shows a second step in a method of inserting the insert into the housing of the aneurysm occlude.
Figure 9:
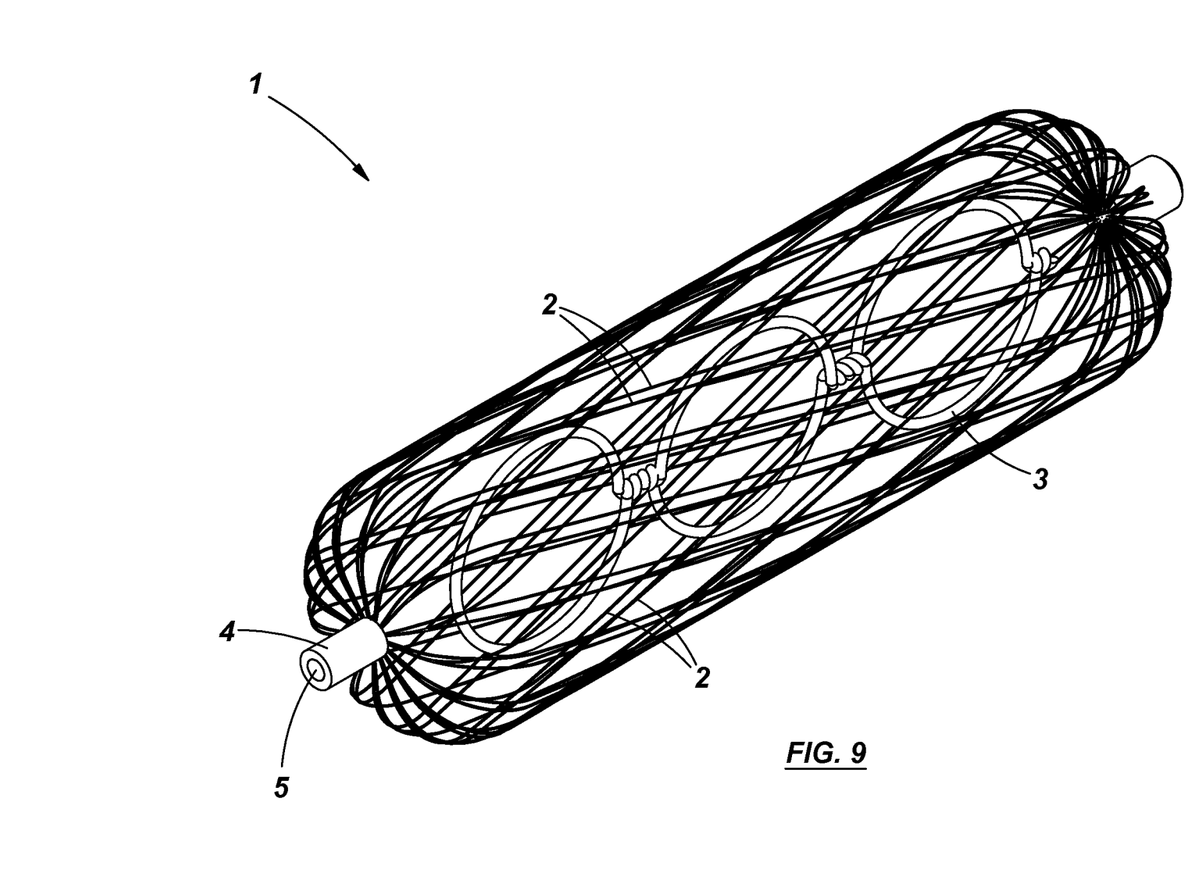
FIG. 9: shows a second embodiment of the occluder.

The stainless steel shanks may be modified to be grasped by clawed-forceps during delivery as is shown in FIG. 9. The shanks terminate in bulbous grasping heads. In an alternative embodiment, the shoulders of the occluder may be more rounded as shown.

This invention thus provides an aneurysm occluder which can fill or assist to fill the cavity of an aneurysm. It will be readily appreciated by persons skilled in the art that when the aneurysm occluder 1 is constrained in the aneurysm cavity, the housing and insert slows or inhibits flow of blood and thus promotes thrombosis.

It will be appreciated that many variations are possible with the present embodiment according to the invention without departing from the scope of spirit of the invention.

The invention claimed is:

1. An aneurysm occluder, comprising a resiliently deformable cage and a frame insert disposed inside the cage, wherein the cage is made of a mesh structure that is cylindrical and closed off at opposite ends, and wherein the frame insert is formed from a closed loop wire and is bent over itself to form a plurality of distinct loop sections inside the cage and at least one end of the frame insert is not secured to the cage.

2. The occluder as claimed in claim 1 in which the mesh structure comprises double stranded mesh strands.

3. The occluder as claimed in claim 1 in which the frame insert is resiliently deformable from the bent condition.

4. The occluder as claimed in claim 1 in which the cage comprises sheet inserts or plates at the opposite ends.

5. The occluder as claimed in claim 4 in which the sheets or plates are made of a flat polyurethane or PTFE sheet material.

6. The occluder as claimed in claim 1 in which the opposite ends are closed off with shanks wherein each shank terminates, at its outer end, in a bulbous gripping member.

7. The occluder as claimed in claim 6 in which the bulbous gripping members facilitate grasping thereof by clawed forceps during delivery, in use.

8. A method of manufacturing an aneurysm occluder of claim 1, comprising the steps of providing a closed off double stranded mesh cage with shanks, inserting a deformable frame insert within the mesh cage, and manufacturing the frame insert by bending a frame over itself to form distinct sections therein.

9. The occluder as claimed in claim 1 in which the frame insert has sheet material attached therein.

* * * * *